United States Patent [19]

Chen et al.

[11] Patent Number: 5,766,865
[45] Date of Patent: Jun. 16, 1998

[54] CELL LINES CAPABLE OF DETECTING LOW LEVELS OF CYTOKINES IN BIOLOGICAL FLUIDS

[75] Inventors: Mann-Jy Chen, Wayne; Paul Chih-Hsueh Chen, Philadelphia, both of Pa.

[73] Assignee: Thomas Jefferson University, Philadelphia, Pa.

[21] Appl. No.: 687,640

[22] Filed: Jul. 26, 1996

[51] Int. Cl.$^6$ .................................................. G01N 33/567
[52] U.S. Cl. ........................ 435/7.21; 435/29; 435/172.3; 435/357
[58] Field of Search ................................. 435/69.1, 70.1, 435/240.2, 172.1, 6, 7.2, 7.21, 29, 172.3, 357

[56] References Cited

U.S. PATENT DOCUMENTS 5,259,046  11/1993  Capon et al. ........................... 536/23.4

OTHER PUBLICATIONS

Stratagene Catalog, 1994, especially p. 223.
Schall, T.J. et al., 1990, Cell vol. 61 pp. 361–370.
Aderka et al., "Increased Serum Levels of Soluble Receptors for Tumor Necrosis Factor in Cancer Patients", *Cancer Res.* 1991, 51, 5602–5607.
Aukrust et al., "Serum Levels of Tumor Necrosis Factor–α(TNFα) and Soluble TNF Receptors in Human Immunodeficiency Virust Type 1 Infection –Correlations to Clinical, Immunologic, and Virologic Parameters", *J. Infect Dis.* 1994, 169, 420–424.
Boldin et al., "Self–association of the Death Domains of the p55 Tumor Necrosis Factor (TNF) Receptor and Fas/APO1 Prompts Signaling for TNF and Fas/APO1 Effects", *J. Biol. Chem.* 1995, 270, 387–391.
Branch et al., "A specific and reliable bioassay for the detection of femtomolar levels of human and murine tumor necrosis factors", *Immunol. Methods* 1991, 143, 251–261.
Chen et al., "Mapping the Domain(s) Critical for the Binding of Human Tumor Necrosis Factor–α to Its Two Receptors", *J. Biol. Chem.* 1995, 270, 2874–2878.
Elasser–Beile et al., "Increased Plasma Concentrations for Type I and II Tumor Necrosis Factor Receptors and IL–2 Receptors in Cancer Patients", *Tumour Biol.* 1994, 15, 17–24.

Espevik et al., "A highly sensitive cell line, WEHI 164 clone 13, for measuring cytotoxic factor/tumor necrosis factor from human monocytes", *J. Immunol. Methods* 1986, 95, 99–105.
Gray et al., "Cloning and express of cDNA for human lymphotoxin, a lymphokine with tumour necrosis activity", *Nature* 1984, 312, 721–727.
Kramer et al., "Serum–free in vitro bioassay for the detection of tumor necrosis factor", *J. Immunol. Methods* 1986, 93, 201–206.
Latini et al., "Cytokines in Acute Myocardial Infarction: Selective Increase in Circulating Tumor Necrosis Factor, Its Soluble Receptor, and Interleukin–1 Receptor Antagonist", *J. Cardiovasc. Pharmacol.* 1994, 23, 1–6.
Meager et al., "Assays for tumour necrosis factor and related cytokines", *J. Immunol. Methods* 1989, 116, 1–17.
Morgan et al., "An improved colorimetric assay for tumor necrosis factor using WEHI 164 cells cultured on novel microtiter plates", *J. Immunol. Methods* 1991, 145, 259–262.
Nargi et al., "Optimization of the L–M cell bioassay for quantitizing tumore necrosis tumor α in serum and plasma", *J. Immunol. Methods* 1993, 159, 81–91.
Van Ostade et al.,"Human TNF mutants with selective activity on the p55 receptor", *Nature* 1993, 361, 266–269.
Wallach, D., "Preparations of Lymphotoxin Induce Resistance to Their Own Cytotoxic Effect", *J. Immunol.* 1984, 132, 2464–2469.
Wong et al., "Antiviral properties of TNF" in *Tumor Necrosis Factors: The Molecules and Their Emerging Role in Medicine*, Bruce Beutler ed. Raven, N.Y., N.Y., 1992, pp. 371–381.
Zhang et al., "Site–directed Mutational Analysis of Human Tumor Necrosis Factor–α Receptor Binding Site and Structure–Functional Relationship", *J. Biol. Chem.* 1992, 267, 24069–24075.

*Primary Examiner*—Nancy Degen
*Assistant Examiner*—Irem Yucel
*Attorney, Agent, or Firm*—Law Offices of Jane Massey Licata

[57] ABSTRACT

A method of genetically engineering a cell line capable of detecting bioactive cytokines or growth factors is provided. Cells lines produced by this method and methods of using these cell lines to detect bioactive cytokines or growth factors in a biological fluid are also provided.

3 Claims, No Drawings

CELL LINES CAPABLE OF DETECTING LOW LEVELS OF CYTOKINES IN BIOLOGICAL FLUIDS

INTRODUCTION

This invention was made in the course of research sponsored by the National Institutes of Health. The U.S. Government may have certain rights in this invention.

BACKGROUND OF THE INVENTION

Tumor necrosis factor-α (TNF-α) and lymphotoxin (TNF-β, LT) are related pleiotropic cytokines sharing two identical cell surface receptors and many of the biological activities important in immunoregulation and inflammatory responses. Cancer patients and people chronically infected with pathological agents such as human immunodeficiency virus secrete higher levels of both TNF and soluble TNF receptors as determined by enzyme linked immunosorbent assay. Aderka et al., *Cancer Res.* 1991, 51, 5602–5607; Elsasser-Beile et al., *Tumour Biol.* 1994, 15, 17–24.; Wong et al., "Antiviral properties of TNF" in *Tumor Necrosis Factors: The Molecules and Their Emerging Role in Medicine*, Bruce Beutler ed. Raven, N.Y., N.Y., 1992, p. 371–381; Aukrust et al., *J. Infect. Dis.* 1994, 169, 420–424. Selective increases in circulating TNF, sTNFR and IL-1Ra also occur in acute myocardial infarction. Latini et al., *J. Cardiovasc. Pharmacol.* 1994, 23, 1–6. However, ELISAs used to determine these levels measure total TNF protein and do not distinguish between TNF bound to the soluble receptor and biologically active TNF.

The functional roles of soluble TNF receptors are believed to be two fold: (1) to sequester high level of TNF-α or TNF-β to prevent their toxicity to the host, and (2) to prolong the bioactivity of low levels of TNF needed for certain normal function by protecting them from protease degradation in biological fluids. It is also possible that tumor cells may shed, or induce normal host cells to shed, soluble TNF receptors in order to escape host immune surveillance via TNF antitumor activity. In order to understand the role of TNF and soluble TNFR's in the progression of human diseases which are modulated by TNF, the bioactivity of TNF is a critical parameter to be considered. Since the level of TNF in normal people is very low, a reliable sensitive bioassay capable of detecting subtle changes in TNF bioactivity during disease progression is highly desirable.

A highly sensitive murine cell line, WEHI 164 clone 13, having an $LD_{50}$ (lethal dose killing 50% of cells) of 2 pg/ml rhTNF, was derived by limiting dilution of parental WEHI 164 murine fibrosarcoma cells. Espevik et al., *J. Immunol. Methods* 1986, 95, 99–105. However, it has been reported that the WEHI 164 clone 13 displays progressively lower sensitivity to TNF with serial passages, resulting in both diminished sensitivity and reduced reproducibility of the bioassay. Meager et al., *J. Immunol. Methods* 1989, 116, 1–17. In addition, the semi-attached cells pose a problem for assay reproducibility and require special plates for assay. Morgan et al., *J. Immunol. Methods* 1991, 145, 259–262. Other modified TNF bioassays using L929 or sensitive subclone L928-8 cells resulted in improved sensitivity but none higher than WEHI 164 clone 13. Branch et al., *Immunol. Methods* 1991, 143, 251–261.

Hypersensitive L929 clones have now been developed which can be propagated easily in serum-containing medium in an uninduced state and made to become hypersensitive to hTNF by induction at the time of bioassay. These cell lines have several advantages over other existing cell lines and provide a sensitive, reliable cell line for use in hTNF bioassays with biological fluids.

SUMMARY OF THE INVENTION

An object of the present invention is to provide a method of genetically engineering cell lines capable of detecting bioactive cytokines or growth factors wherein the cells are transfected with an expression vector comprising a human p55 TNF receptor 1 coding sequence driven by an inducible Rous Sarcoma virus promoter and then propagated in serum-containing medium in the absence of isopropyl-b-D-thiogalactopyranoside. In this method, the expression vector further comprises an external ligand binding domain of a receptor for either than tumor necrosis factor or a growth factor or cytokine other tumor necrosis factor.

Another object of the present invention is to provide a cell line prepared in accordance with this method which is capable of detecting bioactive cytokines or growth factors in biological fluids. In a preferred embodiment, the cell line is capable of detecting bioactive levels of human tumor necrosis factor-α and β.

Another object of the present invention is to provide a method of detecting bioactive cytokines or growth factors in a biological sample which comprises incubating a cell line genetically engineered by this method with isopropyl-b-D-thiogalactopyranoside, and assaying a biological sample suspected of containing the bioactive cytokine or growth factor by incubating the sample with the cell line and determining cell death which is indicative of bioactive cytokine or growth factor in the biological sample.

DETAILED DESCRIPTION OF THE INVENTION

Hypersensitive murine L929 cell lines expressing inducible human p55 TNF receptor 1 (hTNFR-1) have been derived. These cells were propagated in serum-containing medium in the absence of isopropyl-b-D-thiogalactopyranoside (IPTG), conditions under which the cells proliferate well but are not sensitive to the low level of cytotoxin often present in culture medium containing serum. After IPTG induction, the cells became at least 50 fold more sensitive to tumor necrosis factor (hereinafter referred to as TNF, which includes TNF-α and TNF-β). These stable sensitive lines are useful in detecting subtle changes in the bioactivity of TNF or TNF-β in human biological fluids during the progression of diseases which are modulated by TNF and provide advantages over other currently available systems for measuring TNF bioactivity.

Standard TNF cytotoxicity assays use L929 cells as target cells due to the ease of propagation and relatively high sensitivity. Gray et al., *Nature* 1984, 312, 721–727. However, this is a murine cell line and its sensitivity is not sufficient for detecting low levels of hTNF in most biological fluids. A limiting dilution method was used to identify L929 subclones and other cells more sensitive to TNF, resulting in the cloning of WEHI 164 clone 13 with an $LD_{50}$ of 2 pg/ml hTNF and L929-8 with an $LD_{50}$ of 6.25 pg/ml. However, the WEHI 164 clone 13 has been reported to display progressively lower sensitivity to TNF with serial passages. Meager et al., *J. Immunol. Methods* 1989, 116, 1–17. In addition, these semi-attached cells require special plates for assay to minimize the problem in assay reproducibility. Morgan et al., *J. Immunol. Methods* 1991, 145, 259–262. Other modified TNF bioassays using L929 or sensitive subclone L929-8 cells resulted in improved sensitivity, but none higher than WEHI 164 clone 13. Nargi et al., *J. Immunol. Methods* 1993, 159, 81–91; Branch et al., *Immunol. Methods.* 1991, 143, 251–261. A modified assay protocol using pretreatment with Actinomycin D and 40° C. assay temperature in medium containing 15% FCS was used to achieve the reported sensitivity with L929-8 cells. However, FCS serum and other sera has been found to contain non-specific cytotoxins which often make assays irreproducible. Kramer et al., *J. Immunol. Methods* 1986, 93, 201–206.

Hypersensitive murine L929 cell lines expressing inducible human p55 TNF receptor 1 (hTNFR-1) have now been derived. Previous attempts to overexpress hTNFR-1 in L929 cells using the constitutive expression vector pCDNA3 (Invitrogen, San Diego, Calif.) driven by cytomegalovirus promoter resulted in no viable clones with increased TNF sensitivity, suggesting spontaneous death of overexpression cell clones. Spontaneous death has also been observed in other cells overexpressing TNFR-1. Boldin et al., *J. Biol. Chem.* 1995, 270, 387–391.

In the present invention, hTNFR-1 is expressed in L929 cells using an inducible expression vector driven by RSV promoter. Upon IPTG induction, these cells have an $LD_{50}$ of 0.6 pg/ml hTNF with a three hour Actinomycin D pre-incubation. This system can also be used to measure other cytokine concentrations at high sensitivity by making hybrid receptor expression constructs with the internal signal transducing domain of hTNFR-1 and the external ligand binding domain of a receptor for any other cytokine or growth factor. Examples of such other cytokines or growth factors include, but are not limited to, interferon-γ (IFN-γ), granulocyte-macrophage colony stimulating factor (GM-CSF), and interleukins such as interleukin-2 (IL-2), interleukin-4 (IL-4), interleukin-5 (IL-5), interleukin-10 and interleukin-12 (IL-12).

Several L929 subclones were isolated by a cloning ring technique and subclone L929-4 with average TNF sensitivity was used to derive the hypersensitive lines of the present invention. Transfection of other L929 subclones with higher TNF sensitivity resulted in only one subclone which was not more sensitive to TNF than those lines derived from L929-4 cells.

Transfected L929 subclones expressing human TNF receptors (hTNFR's) were screened by testing their sensitivity to hTNF-α mutant R32W which is highly specific for hTNFR-1 and binds murine TNF receptors negligibly. Van Ostade et al., *Nature* 1993, 361, 266–269. Several highly sensitive clones were isolated and the expression of hTNFR-1 was verified by flow cytometric analysis using polyclonal hTNFR-1 antibodies. The sensitivities of three transfected clones to R32W mutant were found to be several hundred fold higher than that of the parental L929 cells when assayed without IPTG induction and metabolic inhibitor ($LD_{50}$ of 0.25 ng/ml to 2.5 ng/ml as compared to an $LD_{50}$ of more than 1.28 µg/ml for the parental L929-4 cells). With IPTG induction, the $LD_{50}$ of all three clones decreased to much less than 0.3 ng/ml, while that of the parental cells did not change. These results indicate that the leaky synthesis of hTNFR made these clones sensitive to mutant R32W and their sensitivities are further increased upon the induction of hTNFR-1 with IPTG.

The sensitivity of these clones to wild type hTNF-α which binds both human and murine TNFR-1, but not murine TNFR-2, was then tested. Without IPTG induction, most clones had similar sensitivity toward hTNF-α as the parental cells ($LD_{50}$ of 1 to 3 ng/ml in the absence of metabolic inhibitor). Upon induction with IPTG, the $LD_{50}$ of the three clones decreased to 40–100 pg/ml, which was even further decreased to 0.8–2 pg/ml in the presence of 1 µg/ml of actinomycin D. Under the same conditions, the parental L929-4 cells have an $LD_{50}$ of approximately 160 pg/ml rhTNF-α.

Cytotoxicity assays performed with one of the three transfected clones in serum-free medium in the presence of actinomycin D and IPTG were also performed. In these assays, one of these clones, referred to as L929-4hR1-3 cells, had an $LD_{50}$ of 1.9 pg/ml and 2.7 pg/ml of rhTNF-α and rhTNF-β, respectively. The other two clones gave similar $LD_{50}$s within the sensitivity limit of this type of assay. Neutralizing monoclonal antibodies to hTNF-α and hTNF-β at 1 µg/ml completely neutralized up to 32 pg/ml and 16 pg/ml of their respective antigens.

A serum-free assay is recommended as the standard bioassay, since some serum may contain TNF-like cytotoxin if the animals were infected. In addition, some serum contains non-specific cytotoxin(s) which can produce a cytotoxic effect equivalent to that produced by as much as 20 pg/ml rhTNF-α in the serum used in these assays. However, even without neutralizing monoclonal antibodies to TNF-α and TNF-β, this type of non-specific cytotoxicity can be distinguished, since the parental L929 cells and the L929-4-hR1 clones are equally sensitive to the non-specific cytotoxin, contrary to the rhTNF-α or TNF-β-induced cytotoxicity on these cell lines.

No spontaneous death of these transfected cells upon IPTG induction has been observed. Saturating radioligand receptor binding measurement on L929-4hR1-3 cells indicated that before and after IPTG induction, these cells expressed approximately 800 and 6,000 total TNF receptors (including both human and mouse TNF receptors), respectively, suggesting that the levels of hTNFR-1 expression in these cells are not high enough to cause substantial self association leading to spontaneous cell death but high enough to cause hypersensitivity.

Using cytotoxic response curves as standard curves and the percent protection yielded by neutralizing monoclonal antibodies against rhTNF-α and rhTNF-β, it was estimated that THP-1 culture cells constitutively secreted bioactive TNF-α equivalent to approximately $1.2 \text{ pg}/5 \times 10^5$ cells/ml of rhTNF-α in 24 hr, while Raji cells constitutively secreted bioactive TNF-β equivalent to approximately $83 \text{ pg}/1 \times 10^6$ cells/ml of rhTNF-β in 24 hr. These estimations were performed in the following fashion. THP-1 cell culture condition medium added to 50% of the final assay volume/well, yielded 30% specific killing of L929-4hR1-3 cells which can be neutralized by antibody to rhTNF-α but not that to rhTNF-β (the difference between percent cell survival with and without neutralizing monoclonal antibody to rhTNF-α). This degree of killing is equivalent to that produced by 0.6 pg/ml of rhTNF-α as estimated from the standard curve. Thus, the condition medium was estimated to contain bioactive TNF-α equivalent to approximately 1.2 pg/ml (0.6 pg/ml/0.5=1.2 pg/ml) of hTNF-α. Raji cell culture condition medium added to 1.56% of the final assay volume/well produced 35% killing of L929-4hR1-3 cells which can be neutralized by monoclonal antibody to rhTNF-β but not that to rhTNF-α (the difference between percent cell survival with and without neutralizing monoclonal antibody to TNF-β). The degree of killing is equivalent to that produced by 1.3 pg/ml of rhTNF-β. Thus, the condition medium was estimated to contain bioactive TNF-β equivalent to approximately 80 pg/ml (1.3 pg/ml/0.0156=83 pg/ml) of rhTNF-β. It should be noted that culture cell condition media or plasma may contain TNF or TNF-β inhibitors such as soluble TNF receptors or antibodies which may reduce the bioactivity of TNF.

When compared to the murine WEHI 164 clone 13, the only cell line known to have comparable sensitivity, the human TNFR-1 expressing L929 lines of the present invention have the following advantages. The new cell line has comparable or higher sensitivity under appropriate assay conditions. These cells express human TNF receptor, which can be more efficient for detecting bioactive human TNF, especially for mutants which do not bind murine TNF receptor. In addition, these cells are useful in detecting TNF activity in the presence of a large excess of inhibitors, such as soluble TNF receptors or antibodies to TNF. These cells can be propagated easily in serum-containing culture medium in their uninduced, less sensitive state without loss of viability. Further, these cells are stable with reproducibly high sensitivity and can be regenerated even if phenotypic drift occurs, although this has not been observed. These cell lines can be used to detect low levels of bioactive TNF in biological fluids such as serum, plasma or tissue culture supernatants. With modification of the assay protocol, these lines may show even higher sensitivity to hTNF. For example, cells pre-treated with actinomycin D for three hours after overnight incubation with IPTG and before the addition of TNF at 37° C. had an $LD_{50}$ which was reduced by 2–3 folds to 0.6 pg/ml.

The following nonlimiting examples are provided to further illustrate the invention.

EXAMPLES

Example 1: Reagents

Recombinant hTNF-α ($2\times10^7$ U/mg), hTNF-α mutant R32W expressed in *E. coli*, rhsTNFRs expressed with baculovirus expression system, and rabbit polyclonal antibodies against rhTNF-α and rhsTNFRs were purified in accordance with procedures described by Zhang et al., *J. Biol. Chem.* 1992, 267, 24069–24075; Chen et al., *J. Biol. Chem.* 1995, 270, 2874–2878. Recombinant hTNF-β was expressed using a baculovirus expression system in accordance with procedures described by Chen et al., *J. Biol. Chem.* 1995, 270, 2874–2878 for expressing rshTNFR's. IgGs were purified from rabbit polyclonal antiserum against hTNF and soluble human TNF receptors using an IgG purification kit from Pierce (Rockford, Ill.) according to the manufacturer's protocol. Neutralizing monoclonal anti-hTNF-α (clone 195) and anti-hTNF-β were obtained from Boehringer/Mannheim (Indianapolis, Ind.). According to the manufacturer, 50 ng and 200 ng of each were required to neutralize 1U (50 pg) of hTNF-α and 1U (50 pg) of hTNF-β, respectively.

Example 2: Cells

Cells

THP-1 (human monocytic leukemia cell), Raji (Burkitt lymphoma cell) and L929 (murine fibrosarcoma cell) were obtained from the ATCC (Rockville, Md.). L929 cells were cultured in DMEM with 10% heat-inactivated fetal calf serum (FCS). All other cell lines were cultured in RPMI-1640 medium with 10% heat inactivated FCS. L929 subline L929-4 was isolated by a cloning ring technique and used for transfection with an hTNFR-1 expressing construct as described below.

The LacSwitch inducible mammalian expression system from Stratagene (Cat. #217450, La Jolla, Calif.) was used to derive L929 cells expressing p55 hTNFR-1. The pOPRS-VICAT expression vector contains the Rous sarcoma virus (RSV)-LTR promoter, intron sequences from the SV40, and a Not1 site into which the chloramphenicol acetyl transferase (CAT) reporter gene was inserted. In addition, modified operator sequences from the lac operon were inserted at two points, one behind the TATA box of the RSV promoter and one within the SV40 intron sequences. The operator sequences served as the binding sites for lac repressor translation products derived from mRNA transcribed from co-transfected p3'SS eukaryotic Lac-repressor-expressing vector DNA. The full length hTNFR-1 coding region was PCR amplified from a cDNA clone, using the following two primers with Not1 recognition sequence in their 5' ends. The 3' primer has the peptide coding sequence of an epitope of influenza virus hemagglutinin (HA1) tagged behind the hTNFR-1 coding sequence (below, underlined). 5' primer: CCAGT ACCAG CGGCC GCGAG CTCGG ATCCA CCATG (SEQ ID NO: 1) and 3'primer: TCGAC AAGCG GCCGC TTAAG CGTAA TCTGG AACAT CGTAT GGATA TCTGA GAAGA CTGGG CGC (SEQ ID NO: 2). The PCR products were restricted with Not1 and ligated with Not1 restricted pOPRSVICAT with CAT sequences removed to derive hTNFR-1-expression construct pOPRSVIhR1HA. L929-4 cells were transfected with 4 μg of pOPRSVIhR1HA DNA and 2 μg of p3'SS eukaryotic Lac-repressor-expressing vector DNA per 3.5 cm dish using lipofectin from Gibco/BRL (Gaithersburg, Md.), according to the instruction manual provided, except that transformed clones were selected with 800 μg/ml of G418 (Gibco/BRL, Gaithersberg, Md.) and 400 μg/ml of hygromycin B from Boehringer/Mannheim (Indianapolis, Ind.). Two weeks later, selected transformed foci were cloned, expanded and tested for their sensitivity toward hTNFR-1-specific hTNF-α mutant R32W which binds murine TNF receptors negligibly. Van Ostade et al., *Nature* 1993, 361, 266–269.

Example 3: FACS Analysis of Cell Surface TNF Receptors

Cells of parental L929-4 and L929-4hR1 subclones were plated at $5\times10^5$ cells/well in 2 ml of culture medium containing 5 mM of IPTG, using a 6-well tissue culture plate. After incubating overnight at 37° C. in a humidified 5% $CO_2$ incubator, each well was washed once with 2 ml PBS and the cells covered with 0.5 ml PBS. The cells were scraped off the plate using a rubber policeman and transferred into a 1.5 ml microfuge tube and centrifuged at 5,000 rpm for 3 minutes. Supernatants were removed and 40 μl of 100 fold diluted rabbit polyclonal antiserum against hTNFR-1 in PBS were added and gently but thoroughly mixed. The tubes were left on ice for 30 minutes, washed 3 times with 500 μl PBS-0.1% gelatin followed by incubating with 40 μl of 20 fold diluted goat anti-rabbit IgG coupled with FITC (100 μg/ml, Oncogen Science, Seattle, Calif.) on ice for 30 minutes. After 3 washes with 500 μl PBS-0.1% gelatin and resuspension in 70 μl of the same buffer, the microfuge tubes were wrapped in aluminum foil and kept at 4° C. before flow cytometric analysis using an EPICS Profile Analyzer from Coulter (Hialeah, Fla.).

Example 4: TNF bioassays

Standard bioassays

L929 cells ($4\times10^4$) in 100 μl of culture medium (DMEM-10% heat inactivated FCS) were plated into each well of a flat bottom 96-well tissue culture plate and incubated overnight in a 37° C., 5% $CO_2$ humidified incubator. Duplicate samples of serial 2 fold dilution of TNF in 100 μl of culture medium containing 2 μg/ml of actinomycin D were added to each well and the incubation was continued for 18 hours. For assays without metabolic inhibitor, $1\times10^4$ cells/well were plated and treatment with TNF lasted 48 hours. After TNF treatment, the cells were washed twice with PBS, stained with 0.5% crystal violet in 20% methanol for 15 minutes, followed by thorough washing with tap water and blotted dry with a paper towel. The dye in each well was dissolved in 50 μl of 33% acetic acid for 10 minutes and $A_{570}$ nm determined on a MR5000Dynatec ELISA autoreader in accordance with procedures described by Zhang et al., *J. Biol. Chem.* 1992, 267, 24069–24075.

Serum-free bioassay using L929-4hR1 cells

Target cells ($4\times10^4$) were seeded into the wells of a 96-well microtiter plate in 100 μl of DMEM medium containing 5% heat inactivated FCS and 5 mM IPTG. After overnight incubation at 37° C. in a 5% $CO_2$ incubator, the medium was replaced with M199 medium (Gibco/BRL, Gaithersburg, Md.) containing 0.5% Peptone (Difco Laboratories, Detroit, Mich.), 24 mM HEPES (pH 7.4), 1 μg/ml of actinomycin D, 5 mM of IPTG and varying amounts of hTNF-α or biological fluid to be tested in a final volume of 200 μl. For assays with actinomycin D pretreatment, the cells were incubated with 1 μg/ml of actinomycin D for three hours after overnight induction with IPTG and before the addition of assay samples. The assays plates were incubated at 37° C. in a 5% $CO_2$ incubator for 18 hours. The wells of the assay plates were then washed twice with PBS, stained with crystal violet and $A_{570}$ nm determined on a MR5000 Dynatec ELISA autoreader as described above. In the neutral red staining procedure, described by Wallach, *J. Immunol.* 1984, 132, 2464–2469, at the end of incubation period with assay samples, 50 μl of 0.05% neutral red in 150 mM NaCl diluted from 2% stock solution in water and filtered through a 0.8 μm filter were added directly to each well. The plate was incubated for another 2 hours. Culture medium and neutral red solutions were then removed carefully by aspiration and the cells washed twice with PBS. The dye was then extracted with 100 μl of sodium phosphate-alcohol solution (0.05M $NaH_2PO_4$ in 50% ethanol) for 10 minutes. $A_{570}$ nm was determined using a MR5000 Dynatec ELISA autoreader as described above, except with automatic shaking for 5 seconds. Assays of culture cell condition medium were modified so that the test samples were replaced with 200 μl of serial dilutions of condition medium collected with RPMI-1640 containing 1% FCS and subsequently made to contain 1 μg/ml of actinomycin D and 5 mM of IPTG before bioassay.

---

---

What is claimed is:

1. A method of genetically altering a murine L929 cell line to express human tumor necrosis factor receptor and detect bioactive human tumor necrosis factor comprising:

(a) transfecting murine L929 cells with an expression vector comprising a human p55 TNF receptor 1 coding sequence driven by an inducible Rous Sarcoma virus promoter; and (b) propagating the transfected cells in serum-containing medium in the absence of isopropyl-b-D-thiogalactopyranoside so that the cells proliferate and are not sensitive to low levels of cytotoxin present in culture medium containing serum.

2. A method of detecting bioactive tumor necrosis factor in a biological sample comprising:
   (a) incubating a cell line genetically engineered in accordance with the method of claim 1 with isopropyl-b-D-thiogalactopyranoside so that the cell line becomes at least 50 fold more sensitive to tumor necrosis factor than unaltered murine L929 cells; and
   (b) assaying a biological sample suspected of containing tumor necrosis factor by incubating the sample with the cell line and determining cell death which is a means of detecting bioactive tumor necrosis factor in the biological sample.

3. The method of claim 2 further comprising pre-incubating the cell line with actinomycin D.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 35
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 1:

```
CCAGTACCAG CGGCCGCGAG CTCGGATCCA CCATG                              35
```

( 2 ) INFORMATION FOR SEQ ID NO: 2:

( i ) SEQUENCE CHARACTERISTICS:
        ( A ) LENGTH: 63
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 2:

```
TCGACAAGCG GCCGCTTAAG CGTAATCTGG AACATCGTAT GGATATCTGA

GAAGACTGGG CGC                                                     63
```